United States Patent [19]

Fu et al.

[11] Patent Number: 5,700,445
[45] Date of Patent: Dec. 23, 1997

[54] N-METHYL PIPERAZINE COMPOUNDS HAVING DOPAMINE RECEPTOR AFFINITY

[75] Inventors: Jian-Min Fu, Brampton; Sumanas Rakhit, Mississauga, both of Canada

[73] Assignee: Allelix Biopharmaceuticals, Inc., Mississauga, Canada

[21] Appl. No.: 354,905

[22] Filed: Dec. 12, 1994

[51] Int. Cl.$^6$ .................. A61K 51/00; A61M 36/14
[52] U.S. Cl. .................. 424/1.81; 424/1.11; 424/1.65; 424/1.69; 514/211
[58] Field of Search .................. 424/1.81, 1.11, 424/1.65, 1.69; 514/211, 220, 217; 540/555, 557

[56] References Cited

U.S. PATENT DOCUMENTS

| | | | |
|---|---|---|---|
| 3,539,573 | 11/1970 | Schmutz | 260/268 |
| 3,546,226 | 12/1970 | Schmutz | 260/268 |
| 3,751,415 | 8/1973 | Schmutz | 260/268 |
| 3,758,479 | 9/1973 | Schmutz | 260/268 |
| 3,761,481 | 9/1973 | Nakanishi et al. | 540/551 |
| 3,811,026 | 5/1974 | Kaplan et al. | 544/378 |
| 3,852,446 | 12/1974 | Schmutz et al. | 514/211 |
| 3,884,920 | 5/1975 | Schmutz et al. | 514/872 |
| 3,908,010 | 9/1975 | Schmutz et al. | 514/211 |
| 3,983,234 | 9/1976 | Sayers | 424/250 |
| 4,096,261 | 6/1978 | Horrom et al. | 514/220 |
| 4,097,597 | 6/1978 | Horrom et al. | 514/220 |
| 4,191,760 | 3/1980 | Horrom et al. | 514/220 |
| 4,243,805 | 1/1981 | Protiva et al. | 544/375 |
| 5,354,747 | 10/1994 | Hansen | 514/211 |
| 5,393,752 | 2/1995 | Liegeois et al. | 514/211 |

FOREIGN PATENT DOCUMENTS

| | | | |
|---|---|---|---|
| 873159 | 4/1979 | Belgium. | |
| 1004596 | 12/1992 | Belgium. | |
| 772160 | 11/1967 | Canada | 260/239.11 |
| 1505357 | 12/1967 | France. | |
| 2316438 | 10/1973 | Germany. | |
| 2461137 | 7/1975 | Germany. | |
| 630916 | 7/1982 | Switzerland. | |
| 1177957 | 1/1970 | United Kingdom. | |
| 9517400 | 6/1995 | WIPO. | |

OTHER PUBLICATIONS

Fouche, J., et al.; Bull. Soc. chim.; (8); pp. 3113-3130, Fr., Psychotropic drugs. 11-Piperazino-10,11-dihydrodibenzo [a,d]cyclohe ptene derivatives (1972).
Schmutz, J., et al.; Chim. Ther.; vol. 2 (6); pp. 424-429; Chemical structure and pharmacological activity of a new group of tricyclic neuroleptics. XI. Heterocycles with seven atoms; (1967).
L. Coscia, et al.; Arzneim.-Forsch. (ARZNAD); vol. 25,(8) (1975); pp. 1261-1265; New Tricyclic Enamine Derivatives with CNS Depressant Properties; (1975).
Chemical Abstracts, vol. 68, No. 23; 1968; 105247.
Chemical Abstracts, vol. 73, No. 11; 1970; 56127.
Chemical Abstracts, vol. 80, No. 11; 1974; 59966.
28—Heterocycles, vol. 80, No. 7; 1974; 37156h.

J. P. Tollenaere, et al., Chimica Therapeutica, Jul.-Aug. 1976, vol. 11; No. 4, pp. 293-298; Quantative structure activity relationships (QSAR) in a series of neuroleptic 10-piperazino-dibenzo(b,f)thiepins, ataxia in mice.
Schmutz, et al.; Helvetica Chimica Acta, vol. 50(1), 1967, pp. 245-249, 29, Heterocycles with 7-membered rings. IX. 11-Amino substituted dibenzo [b,f]-1,4-thiazepines and—oxazepines.
Gianai et al Synthesis, 1985, p.550 "A new facile synthesis of 11-oxo-10,11-dihydro-5H-dibenzo[b,e][1,4]diazepines".
Harris et al J Med Chem, 1982, 25:855 "Affinity of 10-(4-methylpiperazino)dibenz[b,f]oxepins for clozapine and spiroperidol binding sites in rat brain".
Klunder et al J Med Chem, 1992, 35:1887 "Novel non-nucleoside inhibitors of HIV-1 reverse transcriptase. tricyclic pyridobenzoxazepinones and dibenzoxazepinones".
de Paulis et al J Med Chem, 1981, 24(9):1021 "Synthesis of clozapine analogues and their affinity for clozapine and spiroperidol binding sites in rat brain".
Sindelar et al Coll. Czechoslov. Chem. Commun., 1977, 42:2231 "Noncataleptic potential neuroleptics: 2-nitro and 2-hydroxy derivatives of 10-(4-methylpiperzino)-10, 11-dihydrodibenzo[b,f]thiepin".

(List continued on next page.)

*Primary Examiner*—John Kight
*Assistant Examiner*—Dameron Jones
*Attorney, Agent, or Firm*—Nikaido, Marmelstein, Murray & Oram LLP

[57] ABSTRACT

Described herein are D4 receptor-selective compounds of the general formula:

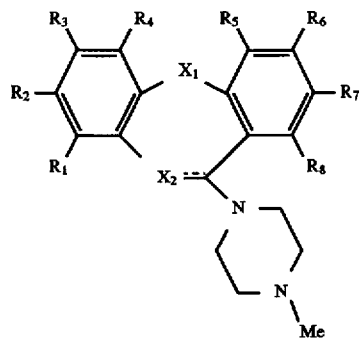

wherein
$X_1$ is selected from $CH_2$, NH, O and S;
$X_2$- - is selected from CH=, $CH_2$13 , and N=;
$R_1$ to $R_8$ are each independently selected from H, $C_{1-4}$alkyl, halo, cyano, nitro and halo-substituted $C_{1-4}$alkyl and acid addition salts, solvates and hydrates thereof. Their use as ligands for dopamine receptor identification and in a drug screening program, and as pharmaceuticals to treat indications in which the D4 receptor is implicated, such as schizophrenia, is also described.

9 Claims, No Drawings

OTHER PUBLICATIONS

Sindelar et al (1978), Collection Czechoslov. Chem. Commun. vol. 43, pp. 309–315. "Non Cataleptic Neuroleptics; 8–chloro–2–hydroxy–11–4(4–methylpiperazino)–5H–dibenzo[b,e,]–1,4–diazepineasaPotentialMetaboliteofClozapine".

Bender et al (1994), Nucl. Med. Biol., vol. 21, No. 7, pp. 921–925. "Synthesis of N.C.A. Carbon–11 Labelled Clozapine and Its Major Metabolite Clozapine–N–Oxide and Comparison of Their Biodistribution in Mice".

Jilek et al (1975), Collection Czechoslov. Chem. Commun, vol. 40 pp. 2887–2904. "Noncataleptic Potential Neuroleptics; 2–Halogeno–10–piperazinodibenzo[b,f]Thiepins".

Valenta et al (1978), Collection Czechoslov. Chem Commun. vol. 41, pp. 3607–3627. "Potential Metabolites of Noncataleptic Neuroleptics: 2–chloro–8–hydroxy–10–(4–methylpiperazino)–and –10–[4–(2–hydroxy–ethyl)piperazino]–10,11–dihydrodibenzo–[b,f] thiepin".

N-METHYL PIPERAZINE COMPOUNDS HAVING DOPAMINE RECEPTOR AFFINITY

This invention relates to compounds that bind to the dopamine D4 receptor, to their preparation and to their use for therapeutic and drug screening purposes.

BACKGROUND OF THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Therefore, it would be desirable to provide compounds that exhibit a high degree of affinity for the D4 receptor.

Some drugs currently on the market exhibit the desired affinity and antagonism for the D4 receptor. Yet because of their structure, these drugs interact also with related dopamine receptors, particularly the D2 receptor type, which results in significant side effects that include altered motor function and tachycardia. It would therefore be desirable to provide compounds that exhibit low affinity for the D2 receptor relative to the D4 receptor, a property herein referred to as D4 selectivity. It would also be desirable to provide compounds that exhibit high affinity and selectivity for the D4 receptor.

Products currently marketed to treat indications in which the D4 receptor function is implicated include the dibenzodiazepine clozapine, and the dibenzoxazepine isoloxapine each incorporating a tricyclic ring system. Analysis of their dopamine receptor binding profile has shown that the preference for binding the D4 receptor relative to the D2 receptor is about 10 fold, for both products. Similarly, both bind the D4 receptor with about the same affinity (Ki of approximately 20 nM). Other products, recently published in the scientific literature, have shown similar D4 to D2 selectivity and D4 affinity values.

It is an object of the present invention to provide a compound having an improved D4 selectivity profile.

It is another object of the present invention to provide a compound having an improved D4 binding affinity.

It is another object of the present invention to provide a compound having both an improved D4 selectivity profile and D4 binding affinity.

It is a further object of the present invention to provide a pharmaceutical composition comprising a compound of the present invention, as active ingredient.

SUMMARY OF THE INVENTION

According to one aspect of the present invention, there are provided compounds of Formula (I):

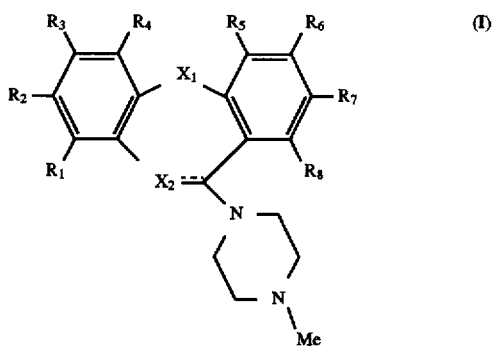

wherein
$X_1$ is selected from $CH_2$, NH, O and S;
$X_{2\text{-}\text{-}}$ is selected from CH=, $CH_2$—, and N=;
$R_1$ to $R_8$ are each independently selected from H, $C_{1\text{-}4}$alkyl, halo, cyano, nitro and halo-substituted $C_{1\text{-}4}$alkyl;
and acid addition salts, solvates and hydrates thereof.

According to another aspect of the invention, there is provided a pharmaceutical composition comprising an effective amount of a compound of Formula I and a pharmaceutically acceptable carrier.

In a further aspect of the invention, there is provided an analytical method in which a compound of the invention is used either to identify dopamine receptors or to distinguish the D4 receptor from the D2 receptor.

These and other aspects of the present invention are now described in greater detail hereinbelow.

DETAILED DESCRIPTION AND PREFERRED EMBODIMENTS

The invention relates to compounds that have a desirable dopamine receptor binding profile ie. those that bind with high affinity to the D4 receptor and/or bind the D4 receptor in a selective manner, relative to the related D2 receptor. According to an aspect of the present invention, there is provided compounds which have affinity or selectivity for D4 receptors, of the Formula (I);

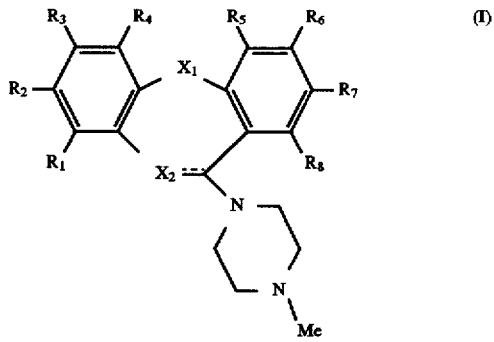

wherein
$X_1$ is selected from $CH_2$, NH, O and S;
$X_{2\text{-}\text{-}}$ is selected from CH=, $CH_2$—, and N=;
$R_1$ to $R_8$ are each independently selected from H, $C_{1\text{-}4}$alkyl, halo, cyano, nitro and halo-substituted $C_{1\text{-}4}$alkyl;
and acid addition salts, solvates and hydrates thereof.

Compounds of the formula (I) are desirably selected from those in which:

$R_2$ and $R_3$ are methyl and $R_1$ and $R_4$ to $R_8$ are H;

$R_5$ is nitro and $R_1$ to $R_4$ and $R_6$ to $R_8$ are H;

$R_2$, $R_3$ and $R_7$ are chloro and $R_1$, $R_4$, $R_5$, $R_6$ and $R_8$ are H;

$R_5$ is chloro and $R_1$ to $R_4$ and $R_6$ to $R_8$ are H;

$R_2$, $R_3$ and $R_5$ are chloro and $R_1$, $R_4$ and $R_6$ to $R_8$ are H;

$R_7$ is trifluoromethyl and $R_1$ to $R_6$ and $R_7$ to $R_8$ are H;

$R_8$ is fluoro and $R_2$ to $R_7$ are H;

$R_5$ is cyano and $R_1$ to $R_4$ and $R_6$ to $R_8$ are H; and $R_2$ is cyano and $R_1$ and $R_3$ to $R_8$ are H.

In accordance with preferred embodiments of the invention, the compounds of formula (I) are selected from:

7,8-dimethyl-11-(4-methyl-1-piperazinyl)-5H-dibenzo[b,e][1,4]diazepine;

4-nitro-11-(4-methyl-1-piperazinyl)dibenz[b,f][1,4]oxazepine;

2,7,8-trichloro-11-(4-methyl-1-piperazinyl)-5H-dibenzo[b,e][1,4]diazepine;

4-chloro-11-(4-methyl-1-piperazinyl)-5H-dibenzo[b,e][1,4]diazepine;

4,7,8-trichloro-11-(4-methyl-1-piperazinyl)-5H-dibenzo[b,e][1,4]diazepine;

2-trifluoromethyl-11-(4-methyl-1-piperazinyl)-5H-dibenzo[b,e][1,4]diazepine;

1-fluoro-11-(4-methyl-1-piperazinyl)-5H-dibenzo[b,e][1,4]diazepine;

4-cyano-11-(4-methyl-1-piperazinyl)dibenz[b,f][1,4]oxazepine; and 2-cyano-10-(4-methyl-piperazinyl)-dibenzo[b,f]thiepine.

Particularly preferred compounds are those that exhibit high affinity for the D4 receptor selected from:

4-chloro-11-(4-methyl-1-piperazinyl)-5H-dibenzo[b,e][1,4]diazepine;

2-cyano-10-(4-methyl-piperazinyl)-dibenzo[b,f]thiepine; and 2-trifluoromethyl-11-(4-methyl-1-piperazinyl)-5H-dibenzo[b,e][1,4]diazepine.

In another particularly preferred embodiment, the compounds exhibit high D4 to D2 receptor selectivity and are selected from:

4-chloro-11-(4-methyl-1-piperazinyl)-5H-dibenzo[b,e][1,4]diazepine;

4-cyano-11-(4- methyl-1-piperazinyl)dibenz[b,f ][1,4]oxazepine;

2-cyano-10-(4-methyl-piperazinyl)-dibenzo[b,f]thiepine;

4-nitro-11-(4-methyl-1-piperazinyl)dibenz[b,f][1,4]oxazepine;

1- fluoro-11-(4-methyl-1-piperazinyl)-5H-dibenzo[b,e][1,4]diazepine;

4,7,8-trichloro-11-(4-methyl-1-piperazinyl)-5H-dibenzo[b,e][1,4]diazepine;

2,7,8-trichloro-11-(4-methyl-1-piperazinyl)-5H-dibenzo[b,e][1,4]diazepine; and 7,8-dimethyl-11-(4- methyl-1-piperazinyl)-5H -dibenzo[b,e][1,4]diazepine.

In the most preferred embodiment, the compounds exhibit both high affinity for the D4 receptor and high D4 to D2 receptor selectivity and are selected from:

4-chloro-11-(4-methyl-1-piperazinyl)-5H-dibenzo[b,e][1,4]diazepine; and 2-cyano-10-(4-methyl-piperazinyl)-dibenzo[b,f]thiepine.

Acid addition salts of the compound of Formula (I) include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates, may be used for example in the isolation of compounds of Formula I for ligand use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those known in the art. A particular process for the preparation of a compound of Formula I or a salt, solvates or hydrate thereof, comprises the step of coupling a tricyclic compound of Formula A:

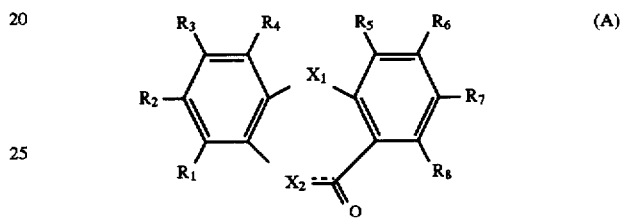

wherein $X_1$, $X_2$--- and $R_1$ to $R_8$ are as defined by Formula (I); with the reagent N-methyl-piperazine (Formula B):

using a Lewis acid such as TiCl or BF3.Et$_2$O

Reagent (A) can be obtained commercially or can be synthesized using established ring closure procedures. For example, when $X_1$ is NH and $X_2$--- is N= (a diazepine), reagent (A) may be prepared according to the procedures described by Giani et al (Synthesis, 1985, 550) by refluxing equimolar amounts of 2-chlorobenzoic acid, o-phenylendiamine and powdered copper in chlorobenzene. The following is a schematic representation of the reaction to obtain the diazepine form of reagent (A):

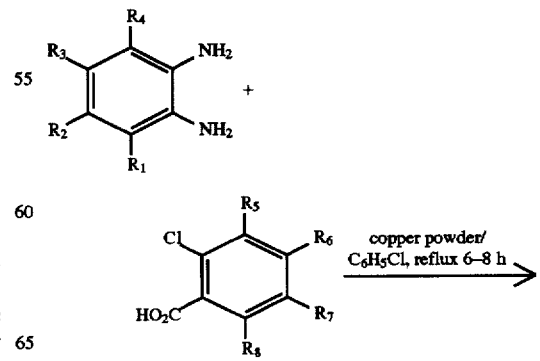

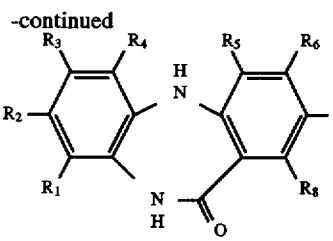

When $X_1$ is O and $X_{2\text{-}\text{-}}$ is N= (an oxazepine), reagent (A) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (A):

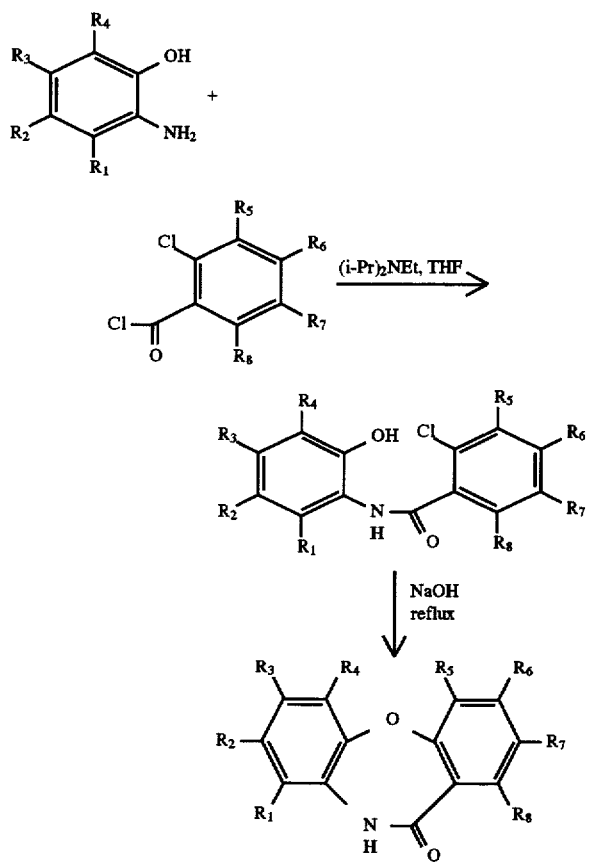

The thiepine form reagent (A), i.e. when $X_1$ is S and $X_2\text{-}\text{-}$ is CH=, may be prepared according to the procedures described by Sindelar et al (Collect. Czech. Chem. Commun, 1983, 48 (4):1187). When reagent (A) is an oxepine i.e. when $X_1$ is O and $X_{2\text{-}\text{-}}$ is $CH_2$—, it may be prepared in the manner reported by Harris et al (J. Med. Chem., 1982, 25(7):855); and the corresponding cycloheptene reagent (A) i.e. when $X_1$ and $X_{2\text{-}\text{-}}$ are both $CH_2$, may prepared as reported by De Paulis et al (J. Med. Chem. 1981, 24(9):1021). The thiazepine reagent (A) may be prepared in a four step process starting from 1-bromo-2-nitrobenzene and methyl thiosalicylate. The steps involve coupling; reduction of the nitro group; hydrolysis of the ester group; and finally ring closure.

For use as a ligand, the present compounds can be stored in packaged form for reconstitution and use. The compounds, and particularly the preferred compounds 4-chloro-11-(4-methyl-1-piperazinyl)-5H-dibenzo[b,e][1,4]diazepine; and 2-cyano-10-(4-methyl-piperazinyl)-dibenzo[b,f]thiepine can be used to distinguish dopamine receptors from other receptor types, for example glutamate and opioid receptors, within a population of receptors and in particular the distinguish the D4 receptor from the D2 receptor. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting the lesser radioactivity, i.e., lesser $^3$H-spiperone binding.

In another embodiment of the invention, the compound is provided in labelled form, such as radiolabelled form e.g. labelled by incorporation within its structure of $^3$H or $^{14}$C or by conjugation to $^{125}$I. Such radiolabelled forms can be used directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

The dopamine receptor binding profile of the present compounds indicates their utility as pharmaceuticals that may be useful for the treatment of various conditions in which the use of a dopamine D4 receptor ligand is indicated, such as for the treatment of anxiety and schizophrenia.

For use in medicine, the compounds of the present invention are usually administered in a standard pharmaceutical composition. The present invention therefore provides, in a further aspect, pharmaceutical compositions comprising an effective amount of a compound of Formula I or a pharmaceutically acceptable salt, solvate or hydrate thereof and a pharmaceutically acceptable carrier.

The compounds of the present invention may be administered by any convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the condition for which administration of a chosen compound is indicated and will of course vary depending on the desired clinical endpoint. It is anticipated that dosage sizes appropriate for administering the compounds of examples 1 and 2 will be roughly equivalent to, or slightly less than, those used currently for clozapine. Accordingly, each dosage unit for oral administration may contain from 1 to about 500 mg, and will be administered in a frequency appropriate for initial and maintenance treatments.

EXAMPLE 1

Preparation of Diazepine and Oxazepine Compounds

4-Chloro-11-(4-methyl-1-piperazinyl)-5H-dibenzo[b,e][1,4]diazepine

To a stirred solution of anisole (0.40 mL, 3.68 mmol) in dry toluene (2.00 mL) was added titanium tetrachloride (0.24 mL, 2.18 mmol) at room temperature under argon. The mixture was then treated with 1-methylpiperazine (1.04 mL, 0.94 g, 9.40 mmol) and 4-chloro-11-oxo-10,11-dihydro-5H-dibenzo[b,e][1,4]diazepine (0.49 g, 2.00 mmol) (Giani et al, supra) and diluted with toluene (1.00 mL). After more 1-methylpiperazine (0.60 mL, 0.54 g, 5.40 mmol) was added, toluene (8.00 mL) was added and the resulting reaction mixture was heated at reflux for 6 h before it was cooled to 60° C. Isopropanol (0.80 mL), celite (0.40 g) and ammonia (30%, 0.50 mL) were added sequentially and the whole mixture was filtered hot. Upon cooling to room temperature, the filtrate was concentrated in vacuo to dryness. The purification was carried out either by acidic (3M HCl) extraction and basification (30% ammonia) or column chromatography using ethyl acetate/methanol (3/1) as the eluent. The title compound was obtained as a light yellow solid in 0.60 g (91%); m.p. 168°–170° C.; MS (EI) 326 (M+).

In a like manner, there was prepared the following additional compounds:

4,7,8-trichloro-11-(4-methyl-1-piperazinyl)-5H-dibenzo[b,e][1,4]diazepine, 69%, m.p. 193°–195° C.; MS 395 (M$^+$1) from (1 mmol) 4,7,8-trichloro-11-oxo-10,11-dihydro-5H-dibenzo[b,e][1,4]diazepine.

2-trifluoromethyl-11-(4-methyl-1-piperazinyl)-5H-dibenzo[b,e][1,4]diazepine, 99%, m.p. 98°–100° C.; MS 361 (M$^+$+1) from (2 mmol) 2-trifluoromethyl-11-oxo-10,11-dihydro-5H-dibenzo[b,e][1,4]diazepine.

7,8-dimethyl-11-(4-methyl-1-piperazinyl)-5H-dibenzo[b,e][1,4]diazepine, 90%, m.p. 155°–158° C.; MS (EI) 320 (M$^+$) from (0.5 mmol) 7,8-dimethyl-11-oxo-10,11-dihydro-5H-dibenzo[b,e][1,4]diazepine.

2,7,8-trichloro-11-(4-methyl-1-piperazinyl)-5H-dibenzo[b,e][1,4]diazepine, 58%, m.p. 182°–185° C.; MS (EI) 394 (M$^+$) from (1 mmol) 2,7,8-trichloro-11-oxo-10,11-dihydro-5H-dibenzo[b,e][1,4]diazepine.

1-fluoro-11-(4-methyl-1-piperazinyl)-5H-dibenz[b,e][1,4]diazepine, 49%, m.p. 146°–147° C.; MS 311 (M$^+$+1) from 1-fluoro-11-oxo-10,11-dihydro-5H-dibenzo[b,e][1,4]diazepine.

4-nitro-11-(4-methyl-1-piperazinyl)dibenz[b,f][1,4]oxazepine from (1.5 mmol) 4-nitro-10,11-dihydrodibenz[b,f][1,4]-oxazepin-11-one (Klunder et al, supra); 53%, m.p. 154°–156° C.; MS 339 (M$^+$+1).

4-cyano-11-(4-methyl-1-piperazinyl)dibenz[b,f][1,4]oxazepine from (0.5 mmol) 4-cyano-10,11-dihydrodibenz[b,f][1,4]-oxazepin-11-one, 99%, m.p. 172°–174° C.; MS 319 (M$^+$+1).

EXAMPLE 2

Preparation of Thiepine Compound 2-cyano-10-(4-methyl-piperazinyl)-dibenzo[b,f]thiepine 2-amino-10-oxo-dibenzo[b,f]thiepine:

To a solution of 2-nitro-10-oxo-dibenzo[b,f]thiepine (2.40 g, 9.30 mmol) (Coll. Czech. Chem. Commun. 1977, 42:2231) in 78% ethanol, was added a solution of CaCl$_2$ (0.66 g, 5.90 mmol) in water (1.00 mL) followed by zinc dust (19.9 g, 30.4 mmol). The reaction mixture was refluxed for 2 h, filtered through celite and washed extensively with hot ethanol. The ethanol filtrate was concentrated to 5.00 mL and water was added to precipitate out the product. The product was filtered and dried under vacuum, purification was performed by recrystallization from EtOAc and hexane, yield 1.97 g (92.3%).

2-cyano-10-oxo-dibenzo[b,f]thiepine:

To a suspension of 2-amino-10-oxo-dibenzo[b,f]thiepine (1 g, 4.40 mmol) in 2N HCl (7.00 mL) at 0° C., was slowly added a solution of NaNO$_2$ , (0.316 g, 4.60 mmol) in water (4.00 mL). A CuCN solution was prepared by heating KCN (1.30 g, 20.0 mmol) in water (5.0 mL) and adding CuSO$_4$.5H$_2$O (1.09 g, 4.40 mmol) solution in water (4.0 mL). Once cooled to room temperature the CuCN solution was slowly added to the diazonium salt mixture and heated to 50° C. for 1 hour. The reaction mixture was diluted with EtOAc and filtered through celite pad. The filtrate was washed with brine, dried (MgSO$_4$) and concentrated to give an oil. The crude material was chromatographed (5%EtOAc/Hexane); yield 0.16 g (15%).

2-cyano-10-(4-methyl-piperazinyl)-dibenzo[b,f]thiepine

To a solution of 2-cyano-10-oxo-dibenzo[b,f]thiepine (0.10 g, 0.40 mmol) in dry toluene (10.00 mL), was added methyl piperazine (0.21 mL, 1.80 mol) followed by the dropwise addition of TiCl$_4$ (1M in toluene, 1.60 mL, 1.6 mol) via syringe. The mixture was stirred at room temperature for 30 min then refluxed for 5 h. The reaction mixture was cooled, dumped into conc $NH_4OH$ and extracted with $CHCl_3$. The combined organic phases were dried ($MgSO_4$) and concentrated in vacuo to dryness. The crude material was chromatographed (20%MeOH/EtOAc) to give 2-cyano-10-(4-methyl-piperazinyl)-dibenzo [b,f]thiepine; yield 0.05 g. (5%).

EXAMPLE 3

Receptor Binding Assay

D2 and D4 receptor-binding affinities of the compounds of examples 1 and 2 were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at −80° C. until used in binding assay. When used in the assay, cells were thawed on ice for 20 min and then 10 ml of incubation buffer (50 mM Tris, 1 mM EDTA, 4 mM $MgCl_2$, 5 mM KCl, 1.5 mM $CaCl_2$, 120 mM NaCl, pH 7.4) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation $CH_4C_1$ (rat pituitary) cells stably transfected with the human D2 receptor (short isoform) were grown in $CO_2$ independent media in roller bottles (1500 cm$^2$) for 10 days. 100 μM $ZnSO_4$ was added to the cells (the D2 promoter being zinc inducible). After 16 hours, fresh media was added to allow the cells to recover for 24 hours. The cells were harvested using versine and then centrifuged in a Sorval centrifuge for 10 minutes, at 5000 rpm (GS3 rotor). Pellets were quickly frozen in liquid nitrogen and stored at −80° C. until used in the binding assays. When used in the assay, cells were thawed on ice for 20 minutes. Each roller bottle produced approximately 72 mg of protein. 10ml of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 μl (50 μg protein) membrane homogenate to a solution of 900 μl incubation buffer and 100 μl (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH 7.4). The filters were then washed 3 times with 5 ml ice cold 50 mM Tris buffer (pH 7.4). Individual filter disks were put in scintillation vials (Biovials, Bechman). Ready Protein Plus liquid scintillant (5 ml, Beckman) was added and the vials counted by liquid scintillation spectrophotometry (Beckman LSC 6500) after equilibrating for three hours at room temperature to determine total binding ($B_T$).

Non-Specific Binding Assay for D4

The incubation was started by the addition of 500 μl (50 μg protein) membrane homogenate to a solution of 400 μincubation buffer, 100 μl $^3$H-spiperone (90 Ci/mmol Amersham diluted in borosilicate glass vial to 0.25 nM final conc.) and 500 μl (30 μM final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 μM (final conc.) of (−) sulpiride (Research Chemicals Inc.) was used in place of dopamine.

Displacement Binding Assay

The incubation was started by the addition to 12×75 mm polypropylene tubes 500 μl (50 μg protein) membrane homogenate to a solution of 400 μincubation buffer, 100 μl (0.25 nM final conc.) $^3$H-spiperone (90 Ci/mmol, Amersham, diluted in borosilicate glass vial) and 500 μof test compound that was prepared from 1 mM stock dissolved in DMSO and stored at −20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value (BD).

Calculations

The test compounds were initially assayed at 1 and 0.1 μM and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/$B_0$ vs concentration of test compound. Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

Assay results are reported in the following Table, and show clearly the advantage in terms of D4 selectivity and or binding affinity of compounds of the invention over clozapine.

D4 AFFINITY

| COMPOUND | Ki (nM) |
|---|---|
| clozapine | 23 |
| 4-chloro-11-(4-methyl-1-piperazinyl)-5H-dibenzo[b,e][1,4]diazepine | 16.7 |
| 2-cyano-10-(4-methyl-piperazinyl)-dibenzo[b,f]thiepine | 4.5 |
| 2-trifluoromethyl-11-(4-methyl-1-piperazinyl)-5H-dibenzo[b,e][1,4]diazepine | 14.2 |

SELECTIVITY FOR D4

| COMPOUND | D2/D4 |
|---|---|
| clozapine | 10 |
| 4-chloro-11-(4-methyl-1-piperazinyl)-5H-dibenzo[b,e][1,4]diazepine | 187.5 |
| 4-cyano-11-(4-methyl-1-piperazinyl)dibenz[b,f][1,4]oxazepine | 64.4 |
| 2-cyano-10-(4-methyl-piperazinyl)-dibenzo[b,f]thiepine | 21.4 |
| 4-nitro-11-(4-methyl-1-piperazinyl)dibenz[b,f][1,4]oxazepine | 21.4 |
| 1-fluoro-11-(4-methyl-1-piperazinyl)-5H-dibenzo[b,e][1,4]diazepine | 12.6 |
| 4,7,8-trichloro-11-(4-methyl-1-piperazinyl)-5H-dibenzo[b,e][1,4]diazepine | 18.8 |
| 2,7,8-trichloro-11-(4-methyl-1-piperazinyl)-5H-dibenzo[b,e][1,4]diazepine | 10.7 |
| 7,8-dimethyl-11-(4-methyl-1-piperazinyl)-5H-dibenzo[b,e][1,4]diazepine | 10.6 |

EXAMPLE 4

Functional Assay

The D4 receptor responds to dopamine and other agonists by reducing adenyl cyclase mediated production of cyclic AMP. Particular test compound 4-chloro-5H-dibenzo[b,e][1,4]diazepine was assayed for its ability to reverse dopamine inhibition of adenyl cyclase by the following procedure. Forskolin was used to elevate the basal adenyl cyclase activity.

CHO Pro 5 cells stably expressing human D4 receptors were plated in 6 well plates in DMEM (Dulbecco's Modified Eagle Medium)/F12(Nutrient Mixture F12 (Ham)) media with 10% FCS (fetal calf serum) and G418 (Geneticen Disulfate), and incubated at 37° C. in a $CO_2$ incubator. The cells were allowed to grow to about 70% confluence before use in the assay.

Antagonist Assay

The culture media of each well was removed by aspiration, and the wells were washed once with serum free media (SFM) (DMEM/F12). Then 2 mL of fresh SFM+IBMX media (SFM with 0.5 mM IBMX (3-isobutyl-1-methylxanthine, 0.1% ascorbic acid and 10 µM pargyline) was added to each well and then incubated at 37° C. for 10 minutes in $CO_2$ incubator. Following incubation, SFM+IBMX media was aspirated and fresh SFM+IBMX media was added to wells separately with one of a) forskolin (10 µM final conc.); b)dopamine and forskolin (both 10 µM final conc.); and c) test compound (1 and 0.1 µM), and dopamine and forskolin (both 10 µM final conc.). Basal adenyl cyclase activity was determined from wells with only SFM+IBMX media added.

The cells were then incubated at 37° C. for 30 minutes in a $CO_2$ incubator. Following incubation the media was aspirated from each well and then washed once with 2 mL of PBS (phosphate buffered saline). Each well was then treated with 1 mL cold 95% ethanol: 5 mM EDTA (2:1) at 4° C. for 1 h. The cells from each well were then scraped and transferred into individual Eppendorf tubes. The tubes were centrifuged for 5 min at 4° C., and the supernatants were transferred to new Eppendorf tubes. The pellets were discarded and the supernatants dried using a SpeedVac. The extracts were then reconstituted in 600 µL of 0.1M sodium acetate buffer, pH 6.1, and stored at 4° C. until assayed for cAMP concentration. cAMP content measured in fmoles/well for each extract was determined by EIA (enzyme-immunoassay) using AmershamBiotrak cAMP EIA kit (Amersham RPN 225).

Total inhibition ($I_0$) of forskolin-stimulated adenyl cyclase activity by dopamine was determined as the difference in concentration of cAMP in the forskolin-treated cells ($C_f$) and dopamine-forskolin treated cells ($C_d$).

$$I_0 = C_f - C_d$$

Net inhibition (I) of forskolin-stimulated adenyl cyclase activity by dopamine in the presence of an antagonist was determined as the difference in concentration of cAMP in the forskolin-treated cells ($C_f$) and test compound, dopamine and forskolin treated cells (C).

$$I = C_f - C$$

The ability of the test compound to reverse the dopamine inhibition (% reversal, %R) was determined by the formula:

| | % REVERSAL OF DOPAMINE EFFECT | |
|---|---|---|
| COMPOUND | 1 µM | 10 µM |
| clozapine | 10 | 62 |
| 4-chloro-11-(4-methyl-1-piperazinyl)-5H-dibenzo | 16 | 58 |

Agonist Assay

To D4 stably expressing CHO cells prepared as previously described were added test compound and forskolin (10 µM final concentration). The cells were incubated, extracted and measured for cAMP concentration as above. Agonist activity of a test compound would result in a decrease in cAMP concentration compared to cells treated with forskolin ($C_f$) only. No decrease was observed, therefore the compound 4-chloro-11-(4-methyl-1-piperazinyl)-5H-dibenzo[b,e][1,4]diazepine exhibited no dopamine agonist activity. It is predicted based on structural and biological functional similarities that the remaining compounds of the invention would also exhibit dopamine antagonist activity.

We claim:
1. A compound of Formula I

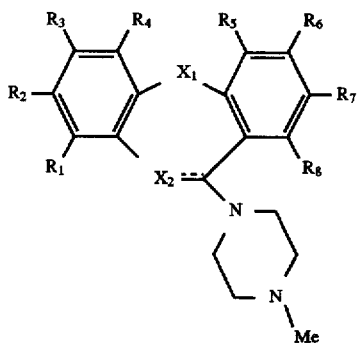

wherein
$X_1$ is NH;
$X_2$--- is N=;
$R_1$ to $R_4$ to $R_8$ are H and $R_5$ is Cl, and
wherein said compound is 4-chloro-11-(4-methyl-1-piperazinyl)-5H-dibenzo[b,e][1,4]diazepine.

2. A pharmaceutical composition, comprising a therapeutically effective amount of a compound according to claim 1, and a pharmaceutically acceptable carrier.

3. A compound according to claim 1, in a radiolabelled form.

4. A pharmaceutical composition for treating a condition mediated by the D4 receptor, comprising a compound according to claim 1 in an amount effective to inhibit the D4 receptor, and a pharmaceutically acceptable carrier thereof.

5. A method for the treatment of a condition mediated by the D4 receptor, comprising the step of administering to a mammal in need of such treatment a composition according to claim 5.

6. A pharmaceutical composition for treating schizophrenia, comprising a compound according to claim 1 in an amount sufficient to produce an antischizophrenia effect, and a pharmaceutically acceptable carrier therefor.

7. A method for the treatment of schizophrenia, comprising the step of administering to a mammal in need of such treatment, a composition according to claim 6.

8. A pharmaceutical composition for treating anxiety, comprising a compound according to claim 1 in an amount sufficient to produce an antianxiety effect, and a pharmaceutically acceptable carrier therefor.

9. A method for the treatment of anxiety, comprising the step of administering to a mammal in need of such treatment, a composition according to claim 8.

* * * * *